(12) United States Patent
McCaffrey et al.

(10) Patent No.: US 11,330,989 B2
(45) Date of Patent: May 17, 2022

(54) MICROCATHETER SENSOR DESIGN FOR MOUNTING SENSOR TO MINIMIZE INDUCED STRAIN

(71) Applicant: Medtronic Vascular, Inc., Santa Rosa, CA (US)

(72) Inventors: Gerry McCaffrey, Ballybrit (IE); Christopher Murphy, Ballybrit (IE); Fiachra Sweeney, Ballybrit (IE); John Kelly, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 680 days.

(21) Appl. No.: 15/077,964

(22) Filed: Mar. 23, 2016

(65) Prior Publication Data

US 2016/0199003 A1 Jul. 14, 2016

Related U.S. Application Data

(63) Continuation-in-part of application No. 14/595,884, filed on Jan. 13, 2015.
(Continued)

(51) Int. Cl.
*A61B 5/0215* (2006.01)
*A61B 5/00* (2006.01)
*A61B 5/02* (2006.01)

(52) U.S. Cl.
CPC ........ *A61B 5/0215* (2013.01); *A61B 5/02007* (2013.01); *A61B 5/6852* (2013.01);
(Continued)

(58) Field of Classification Search
None
See application file for complete search history.

(56) References Cited

U.S. PATENT DOCUMENTS

| 4,718,425 A | 1/1988 | Tanaka et al. |
| 4,771,782 A | 9/1988 | Millar |

(Continued)

FOREIGN PATENT DOCUMENTS

| CN | 101983031 A | 3/2011 |
| DE | 102008045878 | 3/2010 |

(Continued)

OTHER PUBLICATIONS

PCT/US2015/057058, The International Search Report and The Written Opinion of the International Searching Authority.
(Continued)

*Primary Examiner* — Jacqueline Cheng
*Assistant Examiner* — Jairo H Portillo
(74) *Attorney, Agent, or Firm* — Medler Ferro Woodhouse & Mills PLLC (57) ABSTRACT

A catheter, such as a fractional flow reserve catheter, includes an elongate shaft having a proximal end optionally coupled to a handle or luer fitting and a distal end having a distal opening. A pressure sensing wire extends to the distal portion of the elongate shaft to be coupled to a pressure sensor mounted on the distal end for measuring a pressure of a fluid within lumen of vessel. The pressure sensor wire is disposed within a pocket formed adjacent to the pressure sensor thereby minimizing the profile of the catheter. Bending or flexing stress or strain experienced by a pressure sensor mounted to a fractional flow reserve catheter when tracking the catheter through the vasculature creates a distortion of the sensor resulting in an incorrect pressure reading or bend error. In order to isolate the sensor from bending or flexing stress and strain, the sensor is mounted so that the sensor is spaced apart from the elongate shaft of the catheter.

16 Claims, 9 Drawing Sheets

Related U.S. Application Data (60) Provisional application No. 62/012,628, filed on Jun. 16, 2014.

(52) U.S. Cl.
CPC ........... *A61B 5/0084* (2013.01); *A61B 5/6876* (2013.01); *A61B 2562/0247* (2013.01); *A61B 2562/187* (2013.01)

(56) References Cited

U.S. PATENT DOCUMENTS

| | | |
|---|---|---|
| 4,796,641 A | 1/1989 | Mills |
| 4,815,472 A | 3/1989 | Wise |
| 4,850,358 A | 7/1989 | Millar |
| 4,901,731 A | 2/1990 | Millar |
| 4,924,877 A | 5/1990 | Brooks |
| 4,928,693 A | 5/1990 | Goodin |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A | 7/1991 | Lieber et al. |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Corl et al. |
| 5,813,997 A | 9/1998 | Imran et al. |
| 5,827,243 A | 10/1998 | Palestrant |
| 5,873,835 A | 2/1999 | Hastings |
| 5,902,248 A | 5/1999 | Millar et al. |
| 5,964,714 A | 10/1999 | Lafontaine |
| 6,019,728 A * | 2/2000 | Iwata .............. A61B 5/02158 600/486 |
| 6,033,366 A | 3/2000 | Brockway |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A * | 11/2000 | Hammarstrom ..... A61B 5/6851 600/486 |
| 6,167,763 B1 | 1/2001 | Tenerz et al. |
| 6,179,856 B1 | 1/2001 | Barbere |
| 6,182,513 B1 | 2/2001 | Stemme et al. |
| 6,193,669 B1 | 2/2001 | Degany |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 10/2001 | Brockway et al. |
| 6,336,906 B1 | 1/2002 | Hammarstrom et al. |
| 6,354,999 B1 | 3/2002 | Dgany |
| 6,379,308 B1 | 4/2002 | Brockway |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,067 B2 | 9/2003 | Hoek et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 * | 5/2004 | Atsumi .............. A61B 5/0215 600/481 |
| 6,754,608 B2 | 6/2004 | Svanrudh et al. |
| 6,767,327 B1 | 7/2004 | Corl et al. |
| 6,821,287 B1 | 11/2004 | Jang |
| 6,868,736 B2 | 3/2005 | Sawatari et al. |
| 6,926,674 B2 | 8/2005 | Tenerz et al. |
| 6,938,474 B2 | 9/2005 | Melvas |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway |
| 7,060,038 B2 | 6/2006 | Letort et al. |
| 7,097,620 B2 | 8/2006 | Corl et al. |
| 7,112,170 B2 | 9/2006 | Schock |
| 7,134,994 B2 | 11/2006 | Alpert et al. |
| 7,137,953 B2 | 11/2006 | Eigler et al. |
| 7,211,048 B1 | 5/2007 | Najafi |
| 7,222,539 B2 | 5/2007 | Tulkki |
| 7,229,403 B2 | 6/2007 | Schock |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |

(56) References Cited

U.S. PATENT DOCUMENTS

| | | |
|---|---|---|
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,641,639 B2 | 2/2014 | Manstrom |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,860,851 B2 | 10/2014 | Goma et al. |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith |
| 2008/0077085 A1 | 3/2008 | Eidenschink et al. |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Maghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0109104 A1 | 5/2010 | Tiensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0174201 A1* | 7/2010 | Bodecker ............ A61B 5/0031 600/488 |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0265079 A1* | 10/2012 | Hilmersson .......... A61B 5/0215 600/483 |
| 2012/0271178 A1 | 10/2012 | Smith |
| 2012/0278008 A1 | 11/2012 | Davies et al. |

(56) References Cited

U.S. PATENT DOCUMENTS

| | | |
|---|---|---|
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0216481 A1 | 8/2013 | Rosenmeier |
| 2013/0303914 A1 | 11/2013 | Hiltner et al. |
| 2013/0324864 A1 | 12/2013 | Manstrom |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0180141 A1 | 6/2014 | Millett |
| 2014/0187980 A1 | 7/2014 | Burkett |
| 2014/0187984 A1* | 7/2014 | Burkett ............... A61B 5/0215 600/486 |
| 2014/0275892 A1* | 9/2014 | Manstrom ........... A61B 5/0022 600/339 |
| 2014/0276142 A1 | 9/2014 | Dorando |
| 2014/0296687 A1* | 10/2014 | Irazoqui ................. A61B 3/16 600/398 |
| 2014/0379269 A1 | 12/2014 | Schmitt |
| 2015/0032011 A1 | 1/2015 | McGowan et al. |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0066802 A1 | 3/2016 | Keller |
| 2016/0106321 A1 | 4/2016 | Sharma et al. |

FOREIGN PATENT DOCUMENTS

| | | |
|---|---|---|
| EP | 0263190 | 10/1986 |
| EP | 1260175 | 11/2002 |
| EP | 1493381 | 1/2005 |
| EP | 1165171 | 3/2005 |
| EP | 1514512 | 3/2005 |
| EP | 1658808 | 5/2006 |
| EP | 1702641 | 9/2006 |
| EP | 1498068 | 3/2007 |
| EP | 01419796 B1 | 3/2008 |
| JP | 10033488 | 2/1998 |
| JP | 10137199 | 5/1998 |
| JP | 2000-333913 | 12/2000 |
| JP | 2004194996 | 7/2004 |
| JP | 2005-3638066 | 1/2005 |
| JP | 2005-095603 | 4/2005 |
| JP | 2005-3705458 | 8/2005 |
| JP | 2006-204378 | 8/2006 |
| NL | 2009285 | 2/2014 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/0117154 | 11/2006 |
| WO | 2009/111528 A2 | 9/2009 |
| WO | WO2011/120565 | 10/2011 |
| WO | WO2011/0161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | 2015/073423 A1 | 5/2015 |
| WO | 2015/164006 A1 | 10/2015 |
| WO | WO2015/150128 | 10/2015 |
| WO | WO2016/001017 | 1/2016 |

OTHER PUBLICATIONS

PCT/US2017/022637, The International Search Report and The Written Opinion of the International Searching Authority, dated Jul. 12, 2017, 12pages.

Final Office Action in co-pending U.S. Appl. No. 14/920,722, dated Sep. 27, 2018.

International Preliminary Report on Patentability in PCT/US2017/022637, dated Oct. 4, 2018.

Communication pursuant to Article 94(3) EPC issued in European Application No. 15730589.7, dated Jun. 27, 2019.

Office Action dated Apr. 2, 2020, in Chinese Application No. 201580032242.1 (with English Translation).

Office Action Issued Jul. 8, 2020, in Chinese Application No. 201780018289.1 (with English Translation).

* cited by examiner

MICROCATHETER SENSOR DESIGN FOR MOUNTING SENSOR TO MINIMIZE INDUCED STRAIN

RELATED APPLICATIONS

This application is a continuation-in-part of application Ser. No. 14/595,884, filed Jan. 13, 2015, which claims the benefit under 35 U.S.C. § 119 of U.S. Provisional Patent Application No. 62/012,628 filed on Jun. 15, 2014.

FIELD OF THE INVENTION

The invention relates to methods and systems for determining a pressure gradient across a lesion of a vessel for calculating a Fractional Flow Reserve.

BACKGROUND OF THE INVENTION

The severity of a stenosis or lesion in a blood vessel may be assessed by obtaining proximal and distal pressure measurements relative to the given stenosis and using those measurements for calculating a value of the Fractional Flow Reserve (FFR). FFR is defined as the ratio of a first pressure measurement ($P_d$) taken on the distal side of the lesion and to a second pressure measurement taken on the proximal side of the lesion usually within the aorta ($P_a$). Conventionally, a sensor is placed on the distal portion of a guidewire or FFR wire to obtain the first pressure measurement $P_d$, while an external pressure transducer is fluidly connected via tubing to a guide catheter for obtaining the second or aortic (AO) pressure measurement $P_a$. Calculation of the FFR value provides a lesion specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

If an interventional treatment is required, the interventional device, such as a balloon catheter, is tracked over a guide wire to the site of the lesion. Conventional FFR wires generally are not desired by clinicians to be used as guide wires for such interventional devices. Accordingly, if an intervention treatment is required, the clinician generally removes the FFR wire, inserts a conventional guide wire, and tracks the interventional device to the treatment site over the conventional guide wire.

The mounting of a pressure sensor on the distal end of a catheter, such as a microcatheter makes it difficult to isolate the pressure sensor from bending stresses experienced as a result of interaction between the pressure sensor and the housing of the catheter. Due to the high sensitivity and size of the pressure sensor used in this application, any stress placed on the pressure sensor can cause a distortion of the sensor resulting in an incorrect pressure reading or bend error. Accordingly, there remains a need for a microcatheter to obtain pressure measurements suitable for use in calculating an FFR value for a given stenosis, whereby the clinician may use a conventional or preferential guidewire instead of a FFR guidewire. In addition, there remains a need for a FFR microcatheter to minimize both the profile of the catheter and the bending stresses experienced by the pressure sensor.

BRIEF SUMMARY OF THE INVENTION

Embodiments hereof relate to a catheter, such as a pressure measurement catheter, including an elongate shaft having a proximal end optionally coupled to a handle or luer fitting and a distal end having a distal opening. The elongate shaft further includes a proximal portion, an intermediate portion, and a distal portion having a distal tip. In the proximal portion of the elongated shaft, a shaft wall may define two separate lumens: a guide wire lumen and a second or pressure sensor wire lumen, extending parallel to each other or side-by-side along the proximal portion. The distal portion of the elongate shaft is configured to receive a guidewire in a distal portion of guidewire lumen thereof. The pressure sensing wire may extend to the distal portion of the elongate shaft to be coupled to a pressure sensor mounted to a deformable member on the distal tip for measuring a pressure of a fluid within lumen of vessel. The deformable member has adhesive properties and is disposed between the pressure sensor and the catheter. The deformable member reduces the amount of stress and strain transferred to the pressure sensor, thereby reducing distortion of the sensor that may result in an incorrect pressure reading.

Embodiments hereof also relate to a catheter, such as a measurement catheter, including an elongate shaft having a proximal end optionally coupled to a handle or luer fitting and a distal end having a distal opening. The elongate shaft further includes a proximal portion, an intermediate portion, and a distal portion having a distal tip. In the proximal portion of elongated shaft, shaft wall may define two separate lumens: a guide wire lumen and a second or pressure sensor wire lumen, extending parallel to each other or side-by-side along the proximal portion. The distal portion of the elongate shaft is configured to receive a guidewire in a distal portion of the guidewire lumen thereof. The pressure sensing wire lumen may extend to the distal portion of the elongate shaft to be coupled to a pressure sensor mounted to an intermediate member on the distal tip for measuring a pressure of a fluid within lumen of vessel. The intermediate member is disposed between the pressure sensor and the catheter. The intermediate member has a first portion, which is coupled to pressure sensor and a second portion, which is coupled to the catheter. The intermediate member also has a hinge disposed between the first and second portions. When the distal portion of the catheter bends away from the pressure sensor, the catheter does not contact the intermediate member or the pressure sensor because the intermediate member maintains the pressure sensor is a substantially straight configuration relative to the bending catheter. When the distal portion of the catheter bends towards the pressure sensor, the catheter applies a force on the intermediate member. As a result of this force, the first portion of the intermediate member rotates about the hinge in the same direction as the applied force. Since the intermediate member moves the pressure sensor away from the bending catheter, the amount of stress and strain transferred to the pressure sensor is reduced, thereby reducing distortion of the sensor that may result in an incorrect pressure reading.

Embodiments hereof also relate to a catheter, such as a measurement catheter, including an elongate shaft having a proximal end optionally coupled to a handle or luer fitting and a distal end having a distal opening. The elongate shaft further includes a proximal portion, an intermediate portion, and a distal portion having a distal tip. In the proximal portion of elongated shaft, shaft wall may define two separate lumens: a guide wire lumen and a second or pressure sensor wire lumen, extending parallel to each other or side-by-side along the proximal portion. The distal portion of the elongate shaft is configured to receive a guidewire in a distal portion of the guidewire lumen thereof. The pressure sensing wire lumen may extend to the distal portion of the elongate shaft to be coupled to a pressure sensor on the distal tip for measuring a pressure of a fluid within lumen of vessel. Although the pressure sensor is coupled to the distal tip of the catheter, the pressure sensor is suspended above the shaft wall of the catheter by a step extending from the shaft wall. An electrical interconnect (or other wiring) is mounted on the step such that a distal end of the electrical interconnect extends past the step and is disposed within a pocket on the distal tip of the catheter. The pressure sensor is coupled to the distal end of the electrical interconnect and is thereby disposed within the pocket without contacting the shaft wall or the side walls of the pocket. Since the pressure sensor has no contact with the catheter, the amount of stress and strain transferred to the pressure sensor is reduced or even eliminated, thereby reducing distortion of the sensor that may result in an incorrect pressure reading.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. While the disclosure refers to illustrative embodiments for particular applications, it should be understood that the disclosure is not limited thereto. Modifications can be made to the embodiments described herein without departing from the scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "an example," "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" and "distally" are positions distant from or in a direction away from the clinician. "Proximal" and "proximally" are positions near or in a direction toward the clinician.

Figure 1:
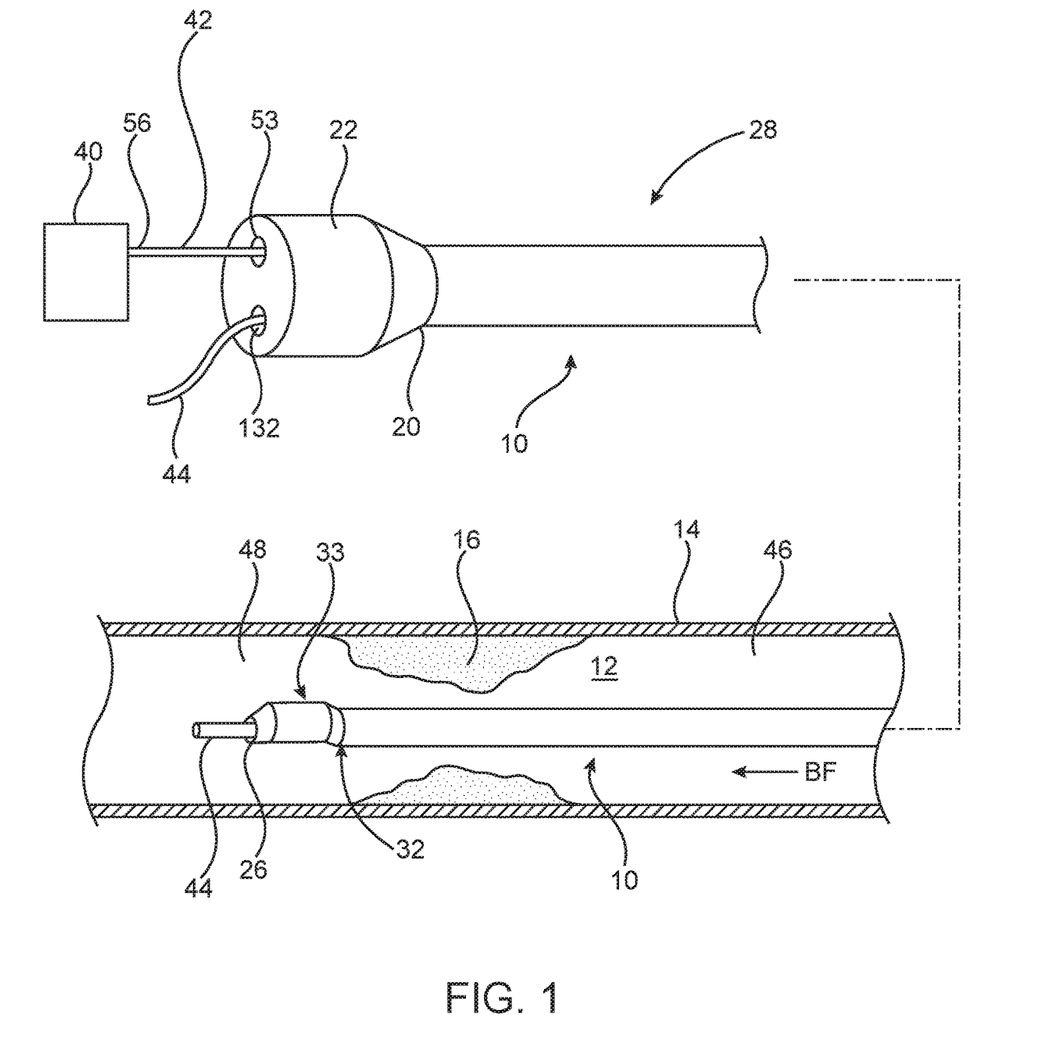
FIG. 1 is a broken view of a system for measuring FFR with a distal portion thereof shown within a vessel including a lesion, the system including a measurement catheter including a pressure sensor and a guidewire, in accordance with an embodiment hereof.

With reference to FIG. 1, a pressure measurement catheter 10 is shown with a proximal portion thereof outside of a patient and a distal portion thereof positioned in situ within a lumen 12 of a patient vessel 14 having a stenosis or lesion 16. In an embodiment hereof, the vessel 14 is a blood vessel such as but not limited to a coronary artery. Lesion 16 is generally representative of any blockage or other structural arrangement that results in a restriction to the flow of fluid through lumen 12 of vessel 14. Lesion 16 may be a result of plaque buildup, including without limitation plaque components such as fibrous, fibro-lipidic (fibro fatty), necrotic core, calcified (dense calcium), blood, fresh thrombus, and mature thrombus. Generally, the composition of lesion will depend on the type of vessel being evaluated. In that regard, it is understood that embodiments hereof are applicable to various types of blockage or other narrowing of a vessel that results in decreased fluid flow.

Figure 2:
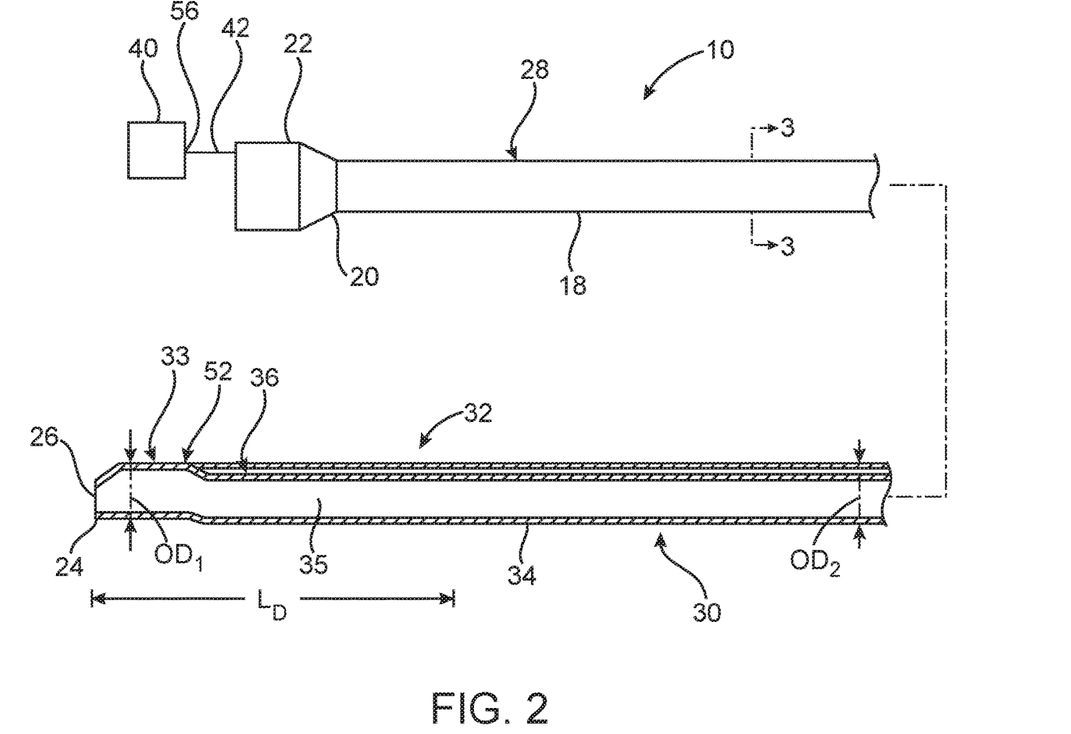
FIG. 2 is a broken view of the catheter of FIG. 1 in partial longitudinal cross-section.

Measurement catheter 10 is shown in FIG. 2 with a distal portion thereof in longitudinal cross-section. Measurement catheter 10 includes an elongate shaft 18 having a proximal end 20 that may be coupled to a handle or luer fitting 22 and a distal end 24 having a distal opening 26. Elongate shaft 18 further includes a proximal portion 28, an intermediate portion 30, and a distal portion 32 having a distal tip 33. Although proximal portion 28, intermediate portion 30, and distal portion 32 of elongate shaft 18 have been described separately, they are described in such a manner for convenience and elongate shaft 18 may be constructed unitarily such that the portions described are part of a unitary shaft. However, different portions of elongate shaft 18 may also be constructed separately and joined together.

In embodiments hereof, elongate shaft 18 or component and/or segments thereof may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. Optionally, the catheter shaft or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of elongate shaft 18 may be formed from a reinforced polymeric tube. In other embodiments of an elongate tubular shaft or component in accordance herewith, a proximal segment thereof may be a hypotube of a medical grade stainless steel with outer and inner tubes of a distal segment thereof being formed from any of the polymeric materials listed above.

Figure 3:
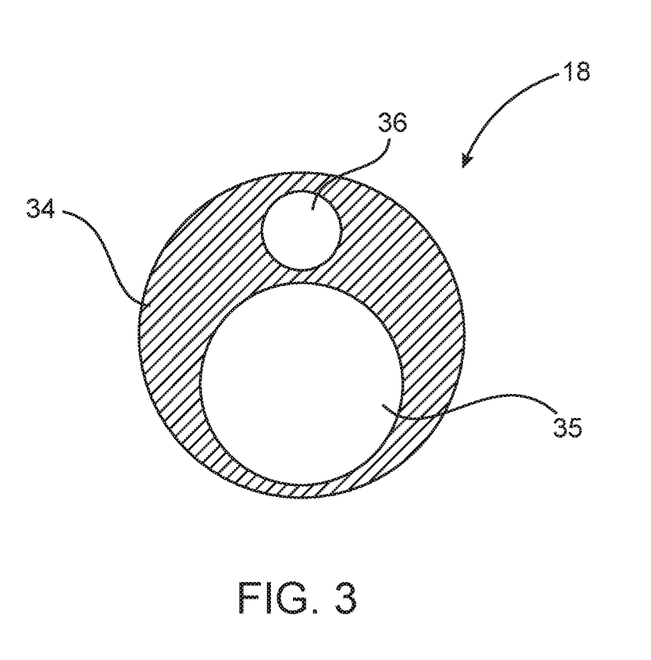
FIG. 3 is a cross-sectional view of the catheter taken along line 3-3 of FIG. 2.
Figure 4:
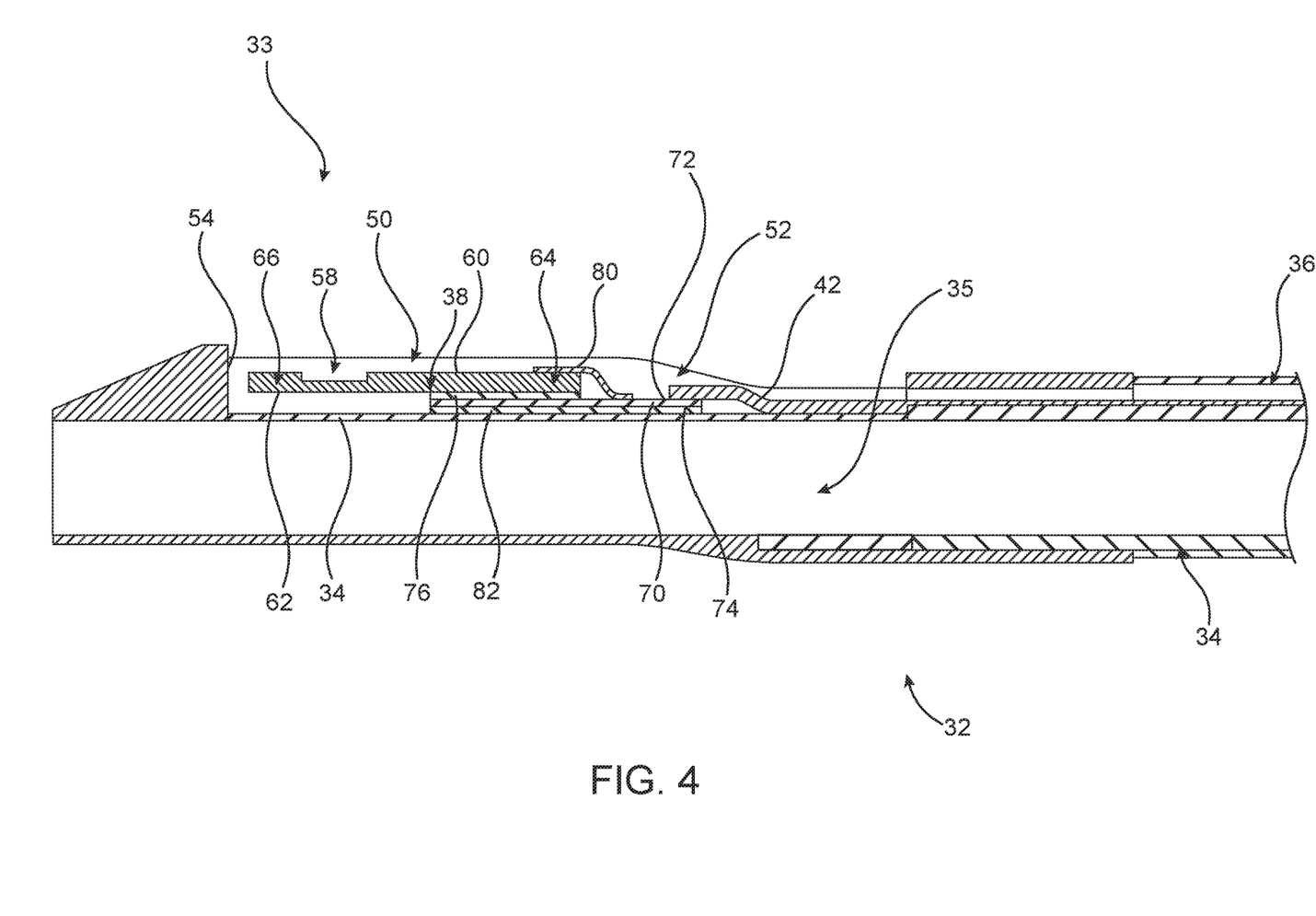
FIG. 4 is a longitudinal cross-sectional view of the distal portion of the catheter of FIG. 1.
Figure 5:
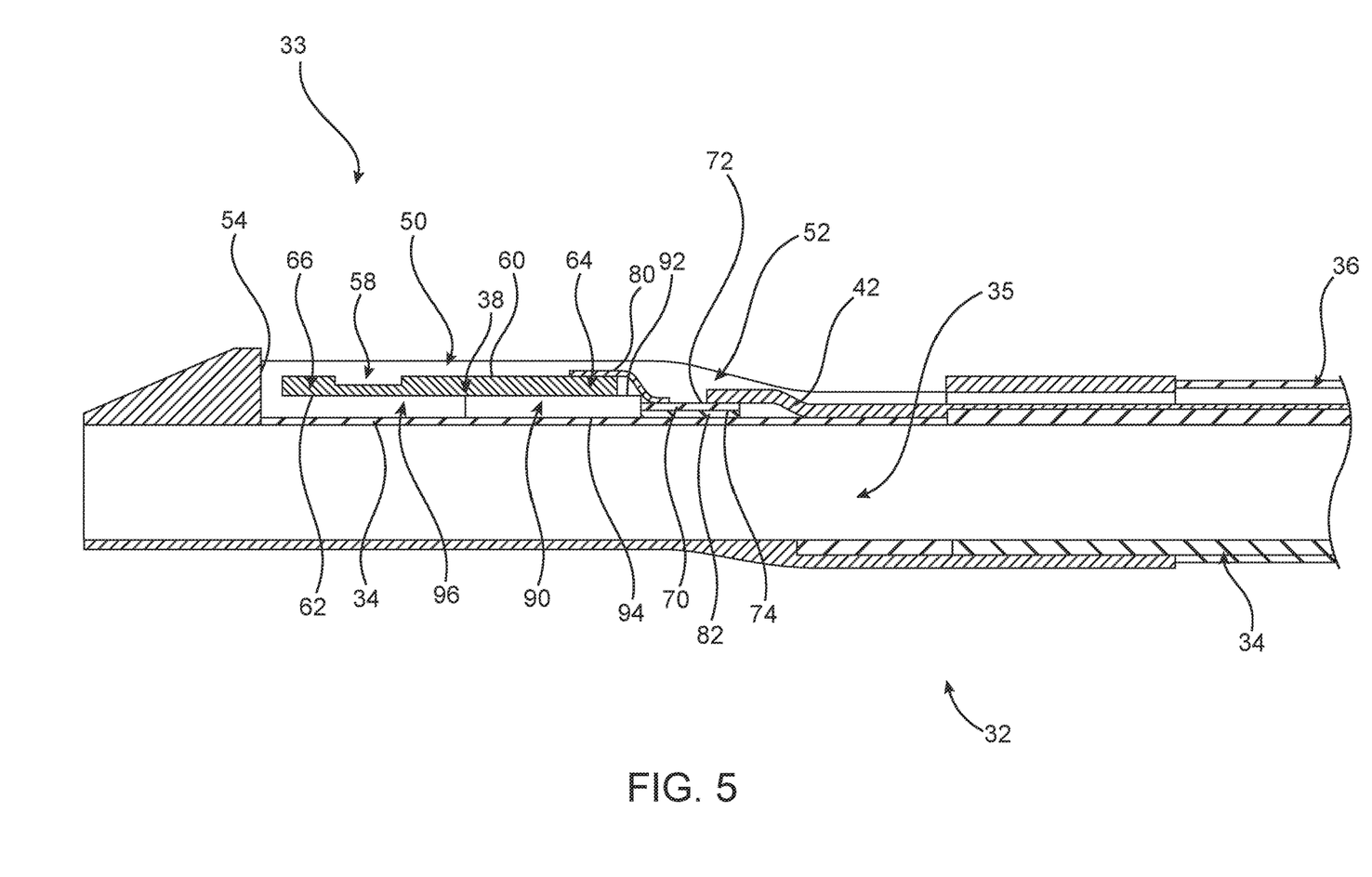
FIG. 5 is a longitudinal cross-sectional view of another embodiment of the distal portion of the catheter of FIG. 1.

As shown in FIGS. 2-3, elongate shaft 18 has a shaft wall 34 defining a guide wire lumen 35 extending therethrough. Guide wire lumen 35 extends through proximal portion 28, intermediate portion 30, and distal portion 32. However, instead of the over-the-wire configuration shown in FIGS. 1-3, catheter 10 may have a rapid exchange configuration wherein guide wire lumen 35 extends through distal portion 32 and intermediate portion 30, and the guidewire exits shaft 18 through a rapid exchange port (not shown) in proximal portion 28, as would be understood by those skilled in the art. In one embodiment, with reference to the cross-sectional view of FIG. 3 (taken along line 3-3 of FIG. 2), in proximal portion 28 of elongated shaft 18, shaft wall 34 defines two separate lumens, guide wire lumen 35 and a second or pressure sensor wire lumen 36, extending parallel to each other or side-by-side along proximal portion 28. Communication wires 42 are omitted in FIG. 3 for clarity. Although depicted as circular in cross-section, one or more lumen(s) of elongated shaft 18 may have any suitable cross-section including for example circular, elliptical, rectangular or crescent-shaped. As explained in more detail below, pressure sensing wire lumen 36 may extend to distal portion 32 of elongate shaft 18 to be coupled to a pressure sensor 38, as shown in FIGS. 4-5. In one embodiment, pressure sensor wire lumen 36 may be eliminated wherein a signal from pressure sensor 38 is sent to a computing device 40 other than via a wire 42 in a dedicated pressure sensor wire lumen 36, such as, but not limited to, wireless transmission or integration of wire 42 into the wall of elongate shaft 18. In other embodiments of an elongate shaft or tubular component in accordance herewith, pressure sensor wire lumen 36 may be eliminated wherein the shaft or a portion thereof may be formed by a tubular polymeric inner liner overlaid with a power lead layer and a polymeric outer jacket. In such an embodiment, the power leads for the respective pressure sensor of the inner shaft may be wrapped around the respective shaft for all or at least a portion of the shaft and secured in position by the polymeric outer jacket so as to be embedded within the shaft. In another such embodiment, the power lead for the respective pressure sensor of the inner shaft may be straight for a section or for the entire length of the shaft, and secured in position against the inner liner by the polymeric outer jacket so as to be embedded within the shaft.

Distal portion 32 of elongate shaft 18 is configured to receive a guidewire 44 in a distal portion of guidewire lumen 35 thereof. Further, as shown in FIG. 1, distal portion 32 is sized to extend from a proximal side 46 of lesion 16, through lesion 16, and to a distal side 48 of lesion 16 such that distal tip 33 is disposed on distal side 48 of lesion 16. Accordingly, in an embodiment, distal portion 32 has a length $L_D$ in the range of 25-300 mm. However, length $L_D$ may be any length suitable such that distal portion 32 may extend from proximal side 46 to distal side 48. Further, because distal portion 32 is configured to extend through lesion 16, the cross-sectional dimension or profile of distal portion 32 is minimized such as to minimize the disruption of blood flow through lesion 16 in order to obtain an accurate FFR measurement.

Distal tip 33 is disposed on distal portion 32 of elongate shaft 18. In an optional embodiment (not shown), distal tip 33 is disposed on intermediate portion 30 of elongate shaft 18 and is located proximally of distal portion 32. Distal tip 33 includes pressure sensor 38 for measuring a pressure of a fluid within lumen 12 of vessel 14, as shown in FIG. 4. In the embodiment shown in FIG. 4, pressure sensor 38 is disposed in a pocket 50 of a thickened portion 52 of distal tip 33. As shown in FIG. 4, pocket 50 may be defined by at least one substantially vertical sidewall 54 and substantially horizontal shaft wall 34. In another embodiment, pocket 50 has at least one sidewall with a curvilinear shape. Pressure sensor 38 may be a piezo-resistive pressure sensor, a piezo-electric pressure sensor, a capacitive pressure sensor, an electromagnetic pressure sensor, an optical pressure sensor, and/or combinations thereof. In one non-limiting example, pressure sensor 38 is a micro electromechanical sensor (MEMS) based pressure die measuring about 240 microns by 70 microns by 1100 microns in size. However, other sized pressure sensors may be used. As shown in FIG. 2, thickened portion 52 needs to accommodate pressure sensor 38. Accordingly, thickened portion 52 of elongate shaft 18 causes tip portion 33 to have an outer diameter $OD_1$ (shown in FIG. 2) which is larger than the outer diameter $OD_2$ of distal portion 32 of elongate shaft 18. However, depending on the size of pressure sensor 38, the outer diameters $OD_1$ and $OD_2$ of the elongate shaft 18 could have substantially the same diameter. In one embodiment, outer diameter $OD_1$ of tip portion 33 is in the range of 0.024 inch-0.040 inch in order to accommodate pressure sensor 38. However, outer diameter $OD_1$ may vary depending on the size of pressure sensor 38, thickness of elongate shaft 18, and other factors used to determine the diameter or profile of shafts. In an optional embodiment, a cover (not shown) could extend substantially over pocket 50 to protect pressure sensor 38 from contacting the vessel wall while still allowing blood flow to surround pressure sensor 38.

Pocket 50 is in communication with pressure sensor wire lumen 36 such that any communication wire(s) 42 from pressure sensor 38 may extend from pocket 50 proximally through pressure sensor wire lumen 36, through a corresponding lumen in luer fitting 22 exiting through proximal port 53 to a computing device 40 coupled to proximal end 56 of communication wire 42. Proximal end 56 of communication wire 42 may be coupled to computing device 40 via various communication pathways, including but not limited to one or more physical connections including electrical, optical, and/or fluid connections, a wireless connection, and/or combinations thereof. Accordingly, it is understood that additional components (e.g., cables, connectors, antennas, routers, switches, etc.) not illustrated in FIG. 1 may be included to facilitate communication between the proximal end 56 of communication wire 42 and computing device 40. In an optional embodiment, computing device 40 is incorporated into catheter 10 or for example, in proximal portion 28.

FIG. 4 is a cross-sectional view of distal tip 33. Therein, sensor 38 has a first surface 60, second surface 62, first end 64 and a second end 66. A diaphragm 58 of sensor 38 is disposed on first surface 60 but in other embodiments, diaphragm 58 cold be disposed anywhere on sensor 38. Communication wires 42 (for example, 0.0025 inch coated copper wire in a tri-filar configuration) extending from lumen 36 are coupled to an electrical interface, such as an interposer 70 which has first and second surfaces 72, 74. In this embodiment, communication wires form an "S-shape", such that one end of the communication wires 42 is raised up to the elevated level of first surface 72 of interposer 70. Second sensor surface 62 is coupled to first surface 72 of interposer 70 (for example, by an adhesive 76), thereby disposing interposer 70 between shaft wall 34 of elongate shaft 18 and sensor 38.

Sensor wires 80 (for example, 0.001 inch gold wires) have a first end coupled to first surface 72 of interposer 70 and a second end coupled to first surface 60 of sensor 38 adjacent to first end 64. Similarly to the communication wires, sensor wires may also make an S-shape, such that one end of the sensor wires 80 is raised up to the elevated level of first surface 60 of sensor 38. Interposer 70 has second surface 74 coupled to shaft wall 34 of elongate shaft 18. In one embodiment, interposer 70 is coupled to shaft wall 34 by an adhesive 82 having a layer depth of about 25 microns. Sensor 38 may be elevated above shaft wall 34 by the thickness of interposer 70 and to some degree by the thickness of the adhesive layers 76 and 82.

FIG. 5 is a cross-sectional view of another embodiment of distal tip 33. Instead of sensor 38 being mounted on interposer 70 as in FIG. 4, sensor 38 is elevated above shaft wall 34 by a deformable member 90 disposed between sensor 38 and shaft wall 34. Deformable member 90 has a first surface 92 and a second surface 94. First surface 92 of deformable member 90 is coupled to sensor 38 along second surface 62 and second surface 94 is coupled to shaft wall 34. In one embodiment, deformable member 90 is any material having a lower durometer than shaft wall 34 in order to minimize the transfer of stress and strain being experienced by shaft wall. In one embodiment, deformable member 90 is coupled to sensor 38 and shaft wall 34 by, for example, an adhesive. However, in another embodiment, deformable member 90 comprises silicone with adhesive properties.

Deformable member 90 elevates sensor 38 above shaft wall 34 by a distance, for example, of about 40-50 microns. In another example, the amount of distance between the sensor 38 and shaft wall 34 is about 25-60 microns. As shown in FIG. 5, sensor 38 is coupled to deformable member 90 at a location that is adjacent first end 64 of sensor 38. Placement of deformable member 90 at this location with respect to sensor 38 creates a pocket 96 under first end 64 of sensor 38, such that first end 64 of sensor 38 is spaced apart from shaft wall 34. In another embodiment, deformable member 90 can extend along any length of second surface 62 of sensor 38. For example, deformable member 90 can extend along substantially the entire length of second surface 62 of sensor 38 such that second end 62 of sensor is not suspended above shaft wall 34. In yet another embodiment, deformable member 90 has a recess (not shown) formed in first surface 92 which is sized to receive sensor 38 therein.

Figure 6A:
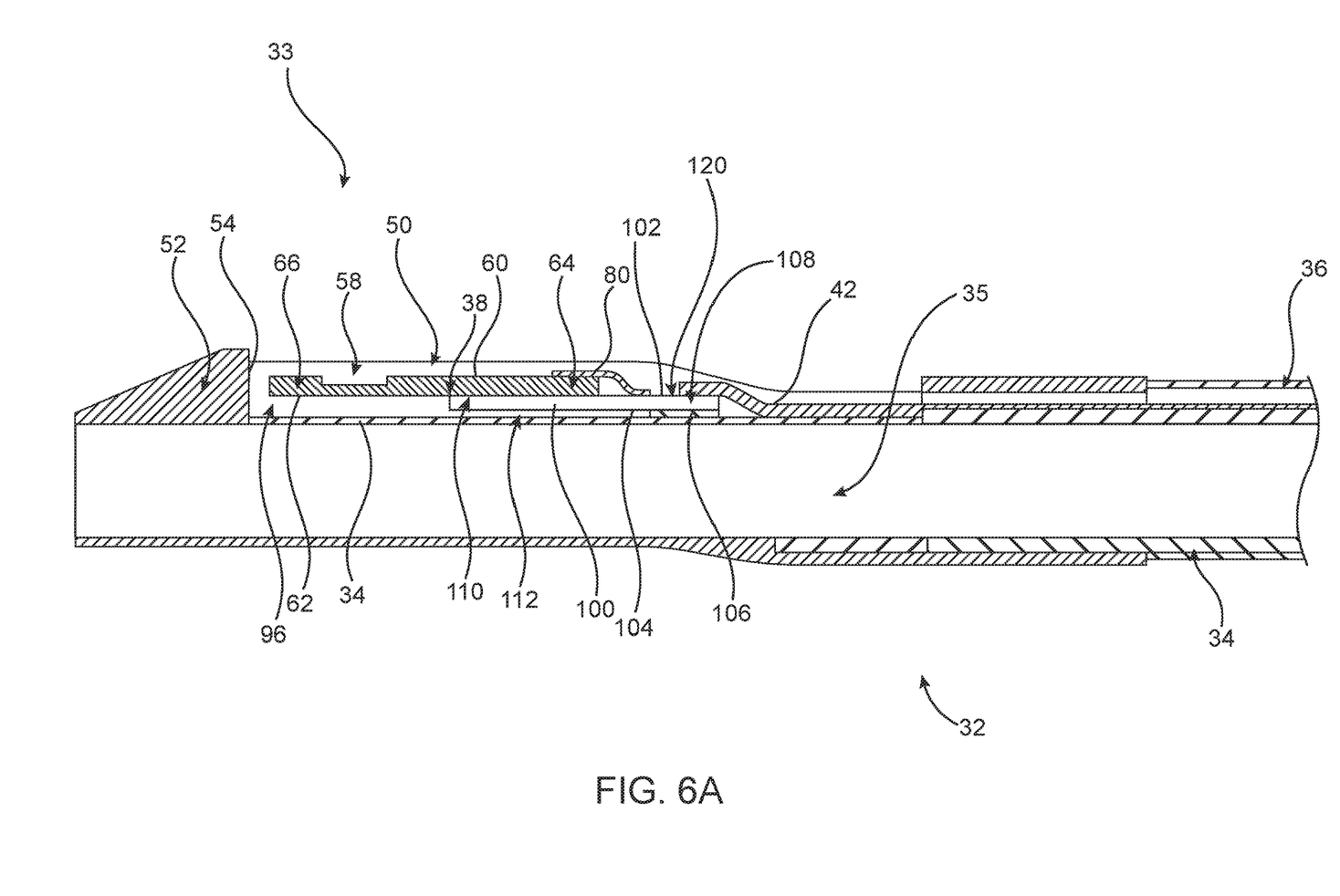
FIG. 6A is a longitudinal cross-sectional view of another embodiment of the distal portion of the catheter of FIG. 1.

FIG. 6A is a cross-sectional view of another embodiment of distal tip 33. Instead of sensor 38 being mounted on interposer 70 as in FIG. 4, sensor 38 is elevated above shaft wall 34 by an intermediate member 100 disposed between sensor 38 and shaft wall 34. Intermediate member 100 has a first surface 102 and a second surface 104. First surface 102 of intermediate member 100 is coupled to sensor 38 along second surface 62 and second surface 104 is coupled to shaft wall 34 by, for example, an adhesive 106. More specifically, as shown in FIG. 6A, intermediate member 100 has a first portion 108 and a second portion 110. First portion 108 is coupled to shaft wall 34 via adhesive 106, while sensor 38 is coupled to second portion 110 along first surface 102. Although FIG. 6A shows first end 64 of sensor 38 coupled to intermediate member 100 with intermediate member 100 extending approximately halfway across second surface 62, intermediate member 100 could extend along any length of second surface 62 of sensor 38.

With first portion 108 of intermediate member 100 coupled to shaft wall 34 by, for example, adhesive 106, intermediate member 100 is elevated above shaft wall forming a second pocket 112. Thus, sensor 38 would be spaced apart from shaft wall 34 by pocket 96, and intermediate member 100 would be spaced apart from shaft wall by second pocket 112, thereby further isolating sensor 38 from the bending stresses and strains of shaft wall 34. In another embodiment, second pocket 112 is eliminated, and instead, second surface 104 of intermediate member 100 extends along shaft wall 34. In the same embodiment, first surface 102 of intermediate member 100 extends along any length of second surface 62 of sensor 38, such as, for example, intermediate member 100 extending approximately halfway across second surface 62 or intermediate member 100 extending along the entire length of second surface 62.

Intermediate member 100 has a hinge 120 on first portion 108. In one embodiment, hinge 120 is a channel on first or second surfaces 102, 104 (or on both first and second surfaces 102, 104) extending transverse to a longitudinal axis of intermediate member 100. In this embodiment, hinge 120 can have a plurality of cross sectional profile shapes, such as rectangular, arcuate or triangular. In other embodiments, hinge 120 can be a living hinge or any type of hinge that allows two portions of intermediate member 100 to rotate relative to each other about a fixed axis of rotation.

Figure 6B:
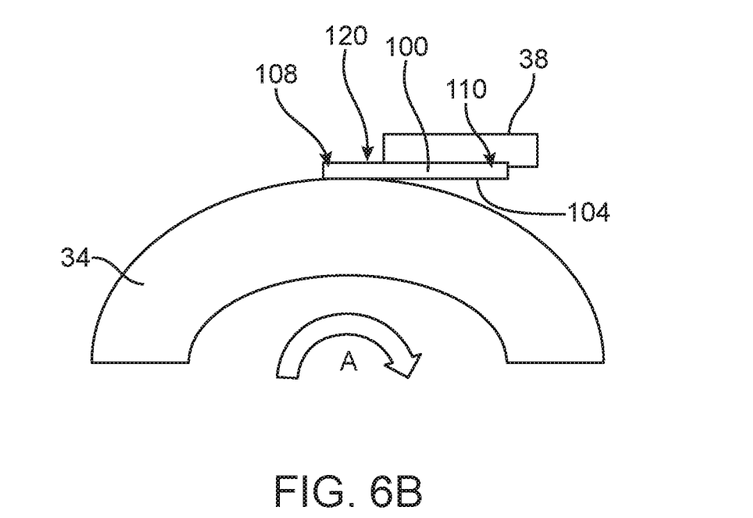
FIG. 6B is an exemplary representation of the distal portion of FIG. 6A under induced stress and strain in the direction of arrow A.
Figure 6C:
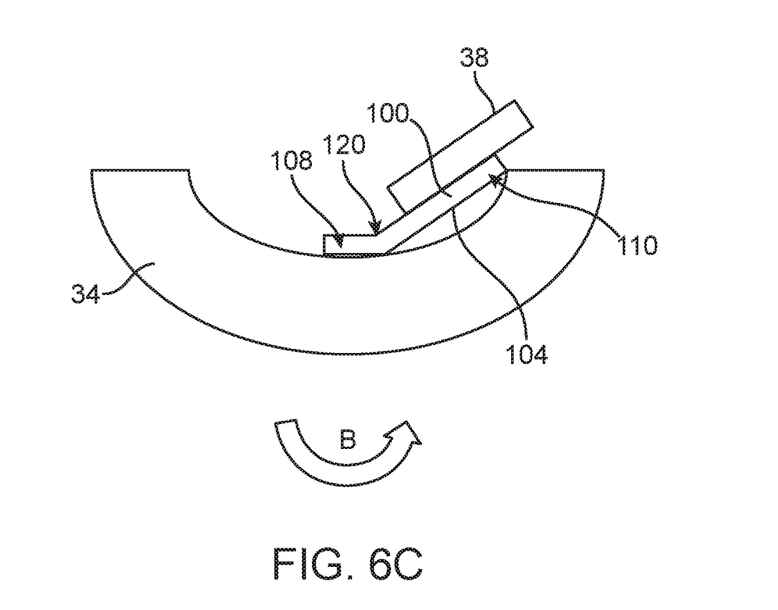
FIG. 6C is an exemplary representation of the distal portion of FIG. 6A under induced stress and strain in the direction of arrow B.

FIGS. 6B-C are exemplary illustrations of shaft wall 34 under bending stress and strain. FIGS. 6B-C are exaggerated to better show the functionality of hinge 120. FIG. 6B shows shaft wall 34 bending or flexing in the direction of arrow A. As can be seen in FIG. 6B, intermediate member 100 remains substantially straight despite shaft wall 34 bending away from intermediate member 100. As a result, sensor 38 also remains substantially straight and is not affected by the bending of shaft wall 34 in the direction of arrow A. In one embodiment, intermediate member 100 is at least as rigid as shaft wall 34. In another embodiment, intermediate member 100 is less rigid that shaft wall 34. However, in either embodiment, intermediate member 100 must be at least rigid enough to maintain sensor in a substantially straight position relative to shaft wall 34.

As shown in FIG. 6C, shaft wall 34 is bending or flexing in the direction of arrow B causing second portion 110 of intermediate member 100 to move in a direction away from shaft wall 34. Specifically, second portion 110 rotates about an axis of rotation provided by hinge 120, wherein the axis of rotation is substantially perpendicular to the longitudinal axis of intermediate member 100. As second portion 110 is rotating about hinge 120, first portion 108 of intermediate member 100 remains coupled to shaft wall 34. Since sensor 38 is coupled to second portion 110 of intermediate member 100, sensor 38 also is rotated about hinge 120. In this way, sensor will maintain being spaced apart from shaft wall 34 thereby preventing stress and strain from being transmitted to sensor 38.

Figure 7A:
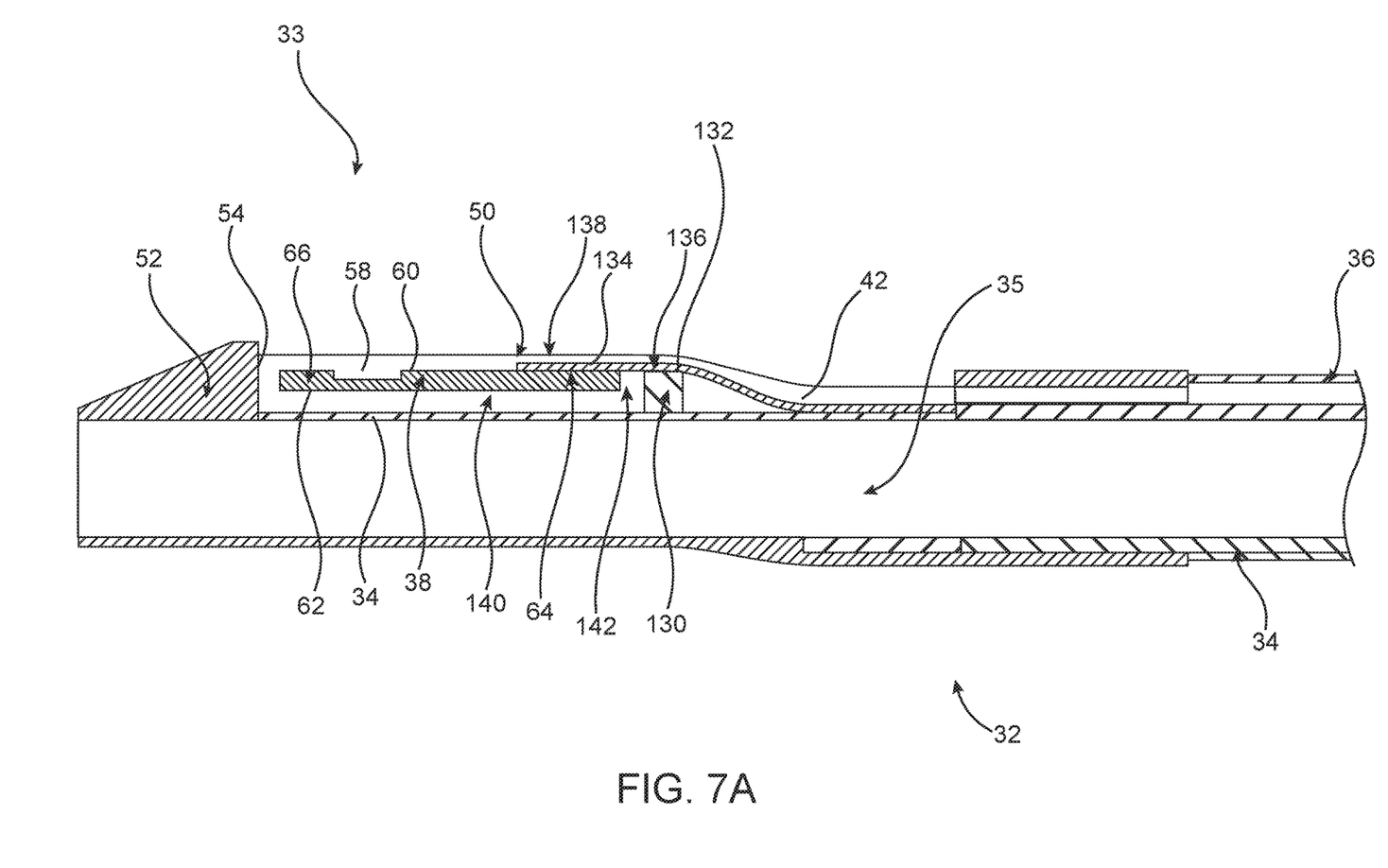
FIG. 7A is a longitudinal cross-sectional view of another embodiment of the distal portion of the catheter of FIG. 1.
Figure 7B:
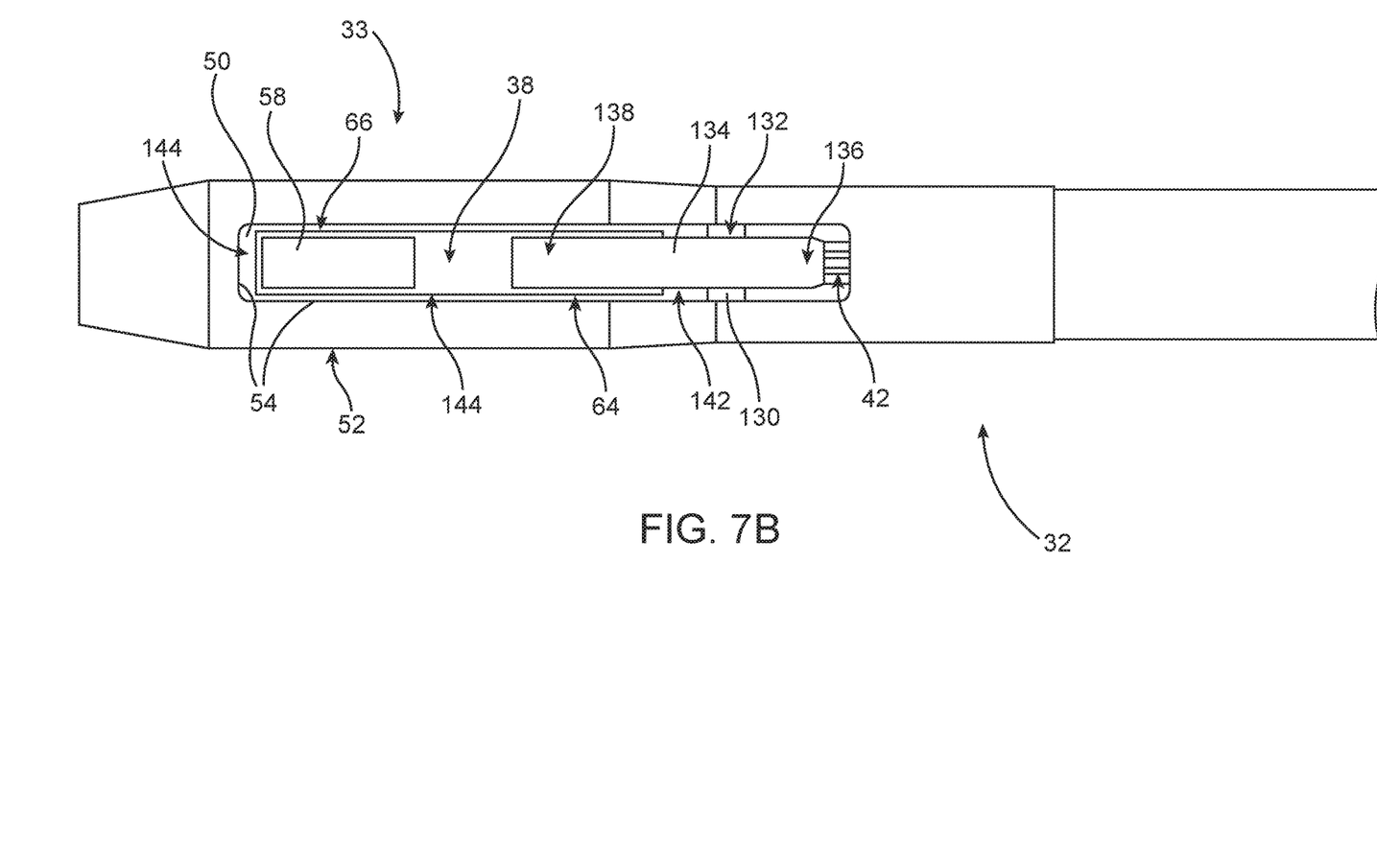
FIG. 7B is a top view of the distal portion of the catheter of FIG. 7A.

FIG. 7A is a cross-sectional view of another embodiment of distal tip 33. FIG. 7B is a top view of distal tip 33 of FIG. 7A. In the embodiment of FIGS. 7A-B, sensor is not mounted to shaft wall 34 but is instead suspended above shaft wall 34 by a step 130. Step 130 extends from shaft wall 34 and has a top surface 132. Communication wiring 42 (or other electrical wiring) or an electrical interconnect 134 is disposed on top surface 132 of step 130. As shown in FIG. 7A, second surface 60 of sensor 38 is coupled to electrical interconnect 134. Specifically, electrical interconnect 134 has a first portion 136 and a second portion 138. First portion 136 of electrical interconnect 134 is coupled to step 130 while second portion 138 is disposed within pocket 50 without contacting shaft wall 34 or sidewalls 54. As shown in FIG. 7A, sensor 38 is coupled to second portion 138 of electrical interconnect 100. In this configuration, sensor 38 is suspended within pocket 50 and therefore does not contact shaft wall 34 or sidewalls 54. The suspended sensor 38 being spaced apart from shaft wall 34 defines a first pocket 140. As shown in FIG. 7A, first end 64 of sensor 38 is spaced apart from step 130 to form a second pocket 142 between sensor 38 and step 130. As shown in FIG. 7B, sensor 38 is spaced apart from side walls 54 to define a third pocket 144 between sensor 38 and side walls 54. Thus, third pocket extends around the outer periphery of sensor 38 as shown in FIG. 7B.

In order to suspend sensor 38 within pocket 50, electrical interconnect 134 needs to be rigid enough to support the weight of sensor 38 and maintain the sensor 38 in a substantially straight configuration relative to shaft wall 34, so as to prevent sensor 38 from contacting shaft wall 34. This is especially the case when shaft wall 34 experiences bending or flexing forces. To better maintain the stability of suspended sensor 38 during bending or flexing, in an optional embodiment, step 130 has grooves or channels (not shown) formed into top surface 132 to receive electrical interconnect 134 (or other electrical or communication wires).

A method of measuring FFR using measurement catheter 10 will now be described with reference to FIG. 1. As would be understood by those skilled in the art, when measuring FFR a guide catheter (not shown) may be advanced through the vasculature such that the guide catheter is disposed within the aorta with a distal end thereof disposed within the aorta at an ostium of the aorta adjacent the branch vessel 14 within which lesion 16 is located. As shown in FIG. 1, guidewire 44 can be advanced intraluminally through the guide catheter, into vessel 14 within lumen 12 to the site of lesion 16. In the embodiment shown, guidewire 44 is advanced from proximal side 46 of lesion 16 to distal side 48 of lesion 16, which is also consistent with the direction of the blood flow BF, as indicated by the arrow BF in FIG. 1. In an embodiment, vessel 14 is a coronary artery, but vessel 14 may be other vessels in which it may be desirable to measure pressure, and in particular, to measure FFR.

Thereafter, as shown in FIG. 1, measurement catheter 10 can be tracked or advanced over indwelling guidewire 44 to the target site such that distal end 32 of elongate shaft 18 is positioned distal of lesion 48. As can be seen in FIG. 1, distal tip 33 including pressure sensor 33 can be disposed distally of lesion 16 such that elongate shaft 18 is disposed through lesion 16.

With measurement catheter 10 in place, pressure sensor 33 measures the pressure of blood distal of the lesion within lumen 12. Accordingly, the pressure measured by pressure sensor 33 is the distal pressure measurement, or $P_d$, used in calculating FFR. In one embodiment, adenosine is administered either intracoronary at the site, bolus, or intravenously by continuous infusion for providing an accurate distal pressure measurement ($P_d$) for an FFR value. A proximal pressure measurement $P_a$, which is taken in the aorta by an external AO pressure transducer associated with the guide catheter, and a simultaneous pressure measurement $P_d$ taken with pressure sensor 33 of measurement catheter 10 are then obtained to provide the FFR value, i.e., $P_d/P_a$, for the lesion. The proximal pressure measurement $P_a$ and distal pressure measurement $P_d$ can be communicated to computing device 40. Computing device 40, shown schematically in FIGS. 1 and 2, may include such components as a CPU, a display device, an amplification and filtering device, an analog-to-digital converter, and various other components. Computing device 40 may receive the proximal pressure measurement $P_a$ and distal pressure measurement $P_d$, and may process them to provide a continuous display of FFR measurement.

When the FFR measurement is completed, measurement catheter 10 may then be completely withdrawn from the patient or repositioned in vivo at another lesion and the process repeated. Pressure-sensing catheters in accordance with embodiments hereof may be used for other than providing proximal and distal pressure measurements ($P_a$, $P_d$) for calculating an FFR value. For instance, pressure-sensing catheters in accordance with embodiments hereof may be used to provide an in vivo pressure measurement anywhere along the vasculature, or a particular lesion therein. As well, embodiments hereof may be used to provide in vivo pressure measurements, across a heart valve, venous valve or other valvular location within the body where it may be deemed useful.

The detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the detailed description.

While various embodiments according to the present invention have been described above, it should be understood that they have been presented by way of illustration and example only, and not limitation. It will be apparent to persons skilled in the relevant art that various changes in form and detail can be made therein without departing from the scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment.

What is claimed is:
1. A catheter comprising:
an elongate shaft including a proximal portion and a distal portion, the elongate shaft having a shaft wall, the shaft wall having an outer surface and an inner surface, the shaft wall inner surface defining a guidewire lumen;
an intermediate member having a first portion at a proximal end and a second portion at a distal end, wherein the first portion is coupled to the shaft wall outer surface at a distal end of the elongate shaft such that the second portion is elevated above the shaft wall and unsupported, forming a second pocket between the second portion and the shaft wall, the intermediate member having a hinge disposed between the first portion and the second portion such that the second portion is rotatable about an axis of rotation defined by the hinge, wherein the axis of rotation is transverse to a longitudinal axis of the intermediate member; and a pressure sensor having a first end and a second end, the pressure sensor coupled to the second portion of the intermediate member at the first end such that the second end of the pressure sensor extending distally beyond the distal end of the intermediate member is unsupported and does not contact the shaft wall and forms a first pocket between the pressure sensor and the shaft wall, the pressure sensor having a diaphragm disposed thereon.

2. The catheter of claim 1, wherein the second portion of the intermediate member is configured for rotation about the axis of rotation by bending forces from the shaft wall resulting from when the elongate shaft is tracked to a treatment site within a vasculature.

3. The catheter of claim 1, wherein the second portion of the intermediate member is sufficiently rigid to maintain the sensor in a substantially straight configuration relative to the elongate shaft when the shaft wall bends away from the intermediate member as a result of bending forces from when the elongate shaft is tracked to a treatment site within a vasculature.

4. The catheter of claim 1, wherein the axis of rotation is substantially perpendicular to the longitudinal axis.

5. The catheter of claim 1, wherein the hinge is disposed on at least one of a first surface and a second surface of the intermediate member.

6. The catheter of claim 1, wherein the pocket between the pressure sensor and the shaft wall is formed such that the pressure sensor is surrounded by blood when inserted into vasculature.

7. The catheter of claim 1, wherein the intermediate member is configured to prevent the pressure sensor from contacting the shaft wall when the shaft wall bends towards the pressure sensor as a result of bending forces resulting from when the elongate shaft is tracked to a treatment site within a vasculature.

8. The catheter of claim 1, wherein the first pocket and the second pocket are in fluid communication.

9. A catheter comprising:

an elongate shaft including a proximal portion and a distal portion, the elongate shaft having a shaft wall, the shaft wall having an outer surface and an inner surface, the shaft wall inner surface defining a guidewire lumen;

an intermediate member having a first portion at a proximal end and a second portion at a distal end, wherein the first portion is coupled to the shaft wall outer surface at a distal end of the elongate shaft and the second portion is elevated above the shaft wall and unsupported, the intermediate member having a hinge disposed between the first portion and the second portion such that the second portion is rotatable about an axis of rotation defined by the hinge, wherein the axis of rotation is transverse to a longitudinal axis of the intermediate member;

a pressure sensor having a first side and a second side opposite the first side, the pressure sensor being coupled to the second portion of the intermediate member at the first side;

sensor wires having a first end coupled to the intermediate member and a second end coupled to the pressure sensor at the second side; and communication wires coupled to the intermediate member and extending through the elongate shaft.

10. The catheter of claim 9, wherein the second portion of the intermediate member is configured for rotation about the axis of rotation by bending forces from the shaft wall which are a result from when the elongate shaft is tracked to a treatment site within a vasculature.

11. The catheter of claim 9, wherein the second portion of the intermediate member is sufficiently rigid to maintain the sensor in a substantially straight configuration relative to the shaft when the shaft wall bends away from the intermediate member as a result of bending forces from when the elongate shaft is tracked to a treatment site within a vasculature.

12. The catheter of claim 9, wherein the axis of rotation is substantially perpendicular to the longitudinal axis.

13. The catheter of claim 9, wherein the hinge is disposed on at least one of a first surface and a second surface of the intermediate member.

14. The catheter of claim 13, wherein the sensor has one portion coupled to the first surface of the intermediate member such that another portion of the sensor defines a pocket between the sensor and the shaft wall.

15. The catheter of claim 9, wherein the first end of the sensor wires are coupled to the intermediate member at an electrical interface at an intermediate member first end and the communication wires are coupled to the intermediate member at the electrical interface.

16. The catheter of claim 9, wherein the intermediate member is configured to prevent the pressure sensor from contacting the shaft wall when the shaft wall bends towards the pressure sensor as a result of bending forces resulting from when the elongate shaft is tracked to a treatment site within a vasculature.

* * * * *